United States Patent
Serrano

(10) Patent No.: US 6,977,324 B2
(45) Date of Patent: Dec. 20, 2005

(54) PROCESS FOR PRODUCING ADHESIVE WOUND DRESSINGS

(75) Inventor: Luiz Antonio Serrano, Guararema (BR)

(73) Assignee: Johnson & Johnson Industria E. Comercio LTDA, San Jose Dos Campos (BR)

( * ) Notice: Subject to any disclaimer, the term of this patent is extended or adjusted under 35 U.S.C. 154(b) by 63 days.

(21) Appl. No.: 10/297,317

(22) PCT Filed: Jun. 20, 2001

(86) PCT No.: PCT/BR01/00076
§ 371 (c)(1), (2), (4) Date: Oct. 2, 2003

(87) PCT Pub. No.: WO02/00150
PCT Pub. Date: Jan. 3, 2002

(65) Prior Publication Data
US 2004/0059272 A1 Mar. 25, 2004

(30) Foreign Application Priority Data
Jun. 28, 2000 (BR) .............................................. 0002839

(51) Int. Cl.[7] .................................................. A61F 13/00
(52) U.S. Cl. ............................................. 602/54; 42/43
(58) Field of Search ................................. 602/900, 903, 602/41–59; D24/189; 206/440, 441

(56) References Cited

U.S. PATENT DOCUMENTS

| | | | |
|---|---|---|---|
| 3,531,847 A | * 10/1970 | Wallerstein | .................. 29/411 |
| 3,550,589 A | 12/1970 | Wallerstein | |
| 4,778,153 A | * 10/1988 | Bachman et al. | ........... 283/101 |
| 4,867,821 A | * 9/1989 | Morgan | ....................... 156/152 |
| 5,021,275 A | * 6/1991 | Kim | ........................... 428/40.8 |
| 5,066,299 A | 11/1991 | Bellingham | |
| 5,269,691 A | * 12/1993 | Waldman | ..................... 434/429 |
| 5,531,855 A | * 7/1996 | Heinecke et al. | ........... 156/252 |
| 5,761,982 A | * 6/1998 | Abt et al. | ..................... 83/861 |
| 5,981,823 A | * 11/1999 | Turngren | ...................... 602/58 |
| 6,156,336 A | * 12/2000 | Bracht | ......................... 424/449 |

FOREIGN PATENT DOCUMENTS

| | | |
|---|---|---|
| DE | 12 74 794 B | 8/1968 |
| DE | 91 15 559 U | 4/1992 |
| DE | 195 11 976 A | 10/1996 |
| WO | WO 99 23982 A | 5/1999 |

OTHER PUBLICATIONS

PCT International Search Report for International Appln. No. PCT/BR01/00076, Date of Mailin Sep. 11, 2001.

* cited by examiner

*Primary Examiner*—Kim M. Lewis

(57) ABSTRACT

A process for producing adhesive wound dressings, from a continuous strip (2) affixing a plurality of pads (3), each pad defining an adhesive wound dressing with a respective strip portion (4), each two adjacent strip portions (4) having a common lateral edge (5) and end edges (6) joining the lateral edges (5) of each strip portion (4), and a strip marginal portion (7) being defined between each two adjacent end edges (6), said process comprising the step of cutting, from said continuous strip (2), at least two different types of strip portions (4), which are dimensioned and shaped so that the strip marginal portions (7) be each incorporated as an integral part of a respective strip portion (4).

3 Claims, 1 Drawing Sheet

PROCESS FOR PRODUCING ADHESIVE WOUND DRESSINGS

CROSS-REFERENCE TO RELATED APPLICATIONS

This application claims the benefit of international application Ser. No. PCT/BR01/00076 filed on Jun. 20, 2001.

FIELD OF THE INVENTION

The present invention refers to a process for producing adhesive wound dressings of the type to be applied to wounds on the human skin and obtained from a strip of flexible film containing pads to be seated on the wounded region of the skin.

BACKGROUND OF THE INVENTION

In the market, there are different shapes and dimensions of adhesive wound dressings to be applied to skin wounds and which are usually formed by a strip of a thin flexible film having a non-adhesive face for handling the dressing, and another face provided with adhesive regions and whereto is affixed, usually in a median portion, an absorbent substract in the form of a pad, which will contact the skin in the wounded region. These adhesive wound dressings receive, during manufacture, protective tapes which are releasably adhered to the adhesive regions of the flexible film. The adhesive wound dressings are obtained from a strip of the flexible film already containing a plurality of pads spaced from each other by a predetermined value and covered by the protecting tape, said strip being submitted to a cutting operation during the manufacturing process of the adhesive wound dressings in a proper machine.

In the known processes for producing the adhesive wound dressings, each shape thereof is individually obtained from the same strip of flexible film, by a cutting operation in a proper machine, which is adjusted in relation to the pitch and shape characteristics of the adhesive wound dressing to be cut. For obtaining the adhesive wound dressings in each strip of a determined type of adhesive wound dressing, each pad which forms said dressings is individually placed onto the strip of flexible film, according to a predetermined constant spacing, as a function of the dimension of each dressing, said pads being placed aligned to each other and to the longitudinal axis of the respective strip of adhesive film and at a distance from each other, from the geometrical center of each two consecutive adjacent pads, which is previously defined as a function of the cutting pitch of the machine, which will always cut respecting the same distance between the pads. These positioning requirements result from limitations of the cutting machine.

In the conventional shapes of adhesive wound dressings, which are usually rectangular, each two consecutive adjacent adhesive wound dressings have a common lateral edge and each dressing further presents end edges, which are rounded, so as to allow a better adhesion of said dressing to the user's skin, without the risk of involuntary release therefrom, as it occurs with the rectilinear end edges.

This larger dimensioning in the end edge region generates excess material, which will be eliminated during the cutting operation, resulting in production losses.

In the known process for producing adhesive wound dressings, the continuous strip of flexible film has, adjacent to each of its lateral edges, a marginal strip portion which is discarded upon the cutting thereof from the adhesive wound dressings. These marginal strip portions result in losses which, due to said usually rounded shape of the adhesive wound dressings in its end edges, vary as a function of the shape and degree of roundness of the end edges of said adhesive wound dressings.

DISCLOSURE OF THE INVENTION

Thus, it is an object of the present invention to provide a process for producing adhesive wound dressings with a non-rectangular contour, from a continuous strip of adhesive film, which minimizes material losses, without requiring equipment modifications.

These and other objectives are attained by a process for producing adhesive wound dressings from a continuous strip in the form of a flexible adhesive film and affixing, along the extension of one of its faces, a plurality of pads, which are spaced from each other and aligned along the longitudinal axis of the continuous strip, each pad defining an adhesive wound dressing with a respective strip portion, each two adjacent strip portions having a common lateral edge and end edges joining the lateral edges of each strip portion, and a strip marginal portion being defined between each two adjacent end edges, said process comprising the step of cutting, from said continuous strip, at least two different types of strip portions, which are dimensioned and shaped so that the strip marginal portions be each incorporated as an integral part of a respective strip portion.

BRIEF DESCRIPTION OF THE DRAWINGS

The invention will be described below, based on the attached drawings, in which.

BEST MODE OF CARRYING OUT THE INVENTION

Figure 1:
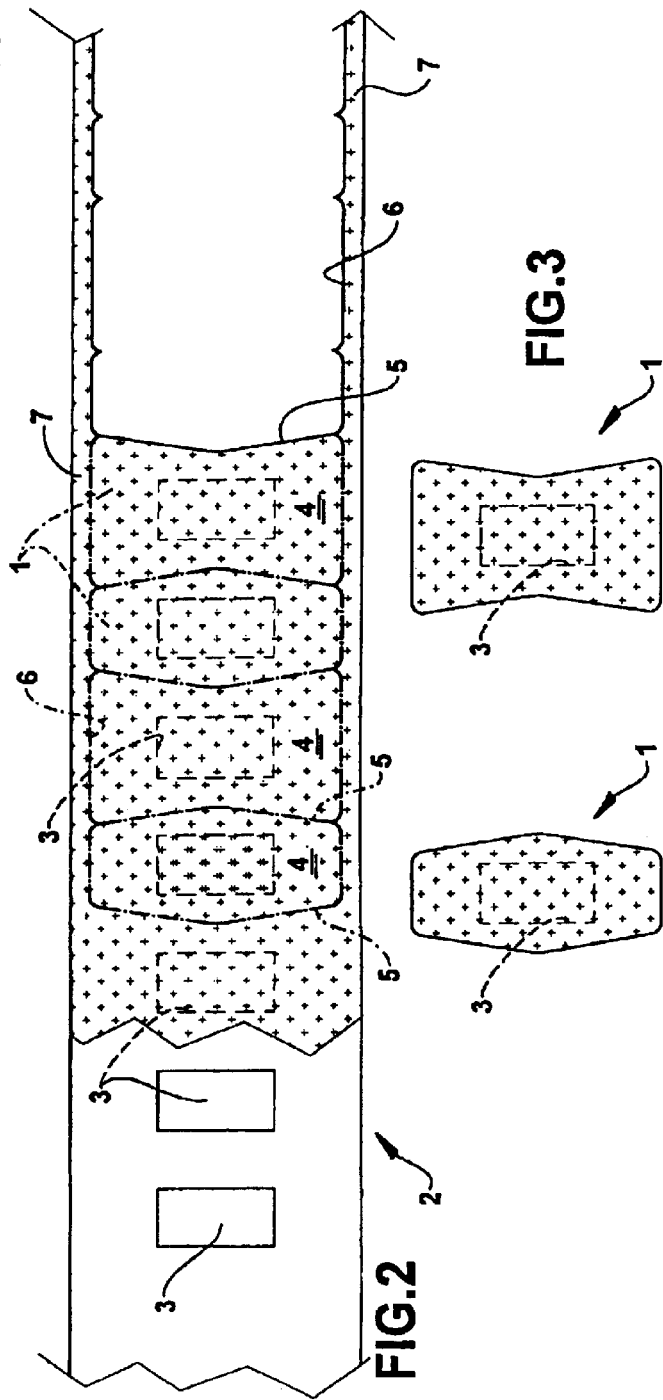
FIG. 1 illustrates, schematically, an upper plan view of a continuous strip, wherefrom are cut adhesive wound dressings, which are represented in said strip, before cutting, in dashed-dotted lines, according to the prior art.

The present invention refers to a process for producing adhesive wound dressings 1 of the type formed from a continuous strip 2, of flexible film, having an adhesive face affixing, along the extension thereof, a plurality of pads 3, which are spaced from each other and aligned along the longitudinal axis of the continuous strip 2, each pad defining, upon cutting the continuous strip 2, with a respective strip portion 4, an adhesive wound dressing 1 and receiving, in a detachable way, protecting tapes (not illustrated), which cover and protect the surface of the plurality of pads 3.

Each strip portion 4 has lateral edges 5 and end edges 6, the latter joining said lateral edges 5 and defining the contour of the respective adhesive wound dressing 1 upon the cutting of the continues strip 2.

In order to produce the adhesive wound dressings 1, each pad 3 is automatically and individually placed along the extension of the adhesive face of the continuous strip 2, spaced from each other by a predetermined constant value, which is calculated as a function of the cutting pitch of a proper machinery.

In each continuous strip 2, each two consecutive adjacent strip portions 4 have a common lateral edge 5, a marginal strip portion 7 being defined between each two adjacent end edges 6, each one associated with a respective strip portion 4.

In the conventional constructions of the prior art adhesive wound dressings (FIG. 1), the process for producing the adhesive wound dressings produces, in the same continuous strip 2, adhesive wound dressings 1 with the same shape, which, as a function of the contour of the adhesive wound dressing, generates losses of the strip material at the; region of the strip marginal portions 7 between two adjacent strip portions 4, wherefrom the adjacent end edges of two strip portions 4 begin.

Regarding the adhesive wound dressings 1 with a substantially rectangular conventional contour, these losses are not very relevant. However, when the adhesive wound dressings 1 have a non-rectangular contour, these losses increase considerably.

Figure 2:
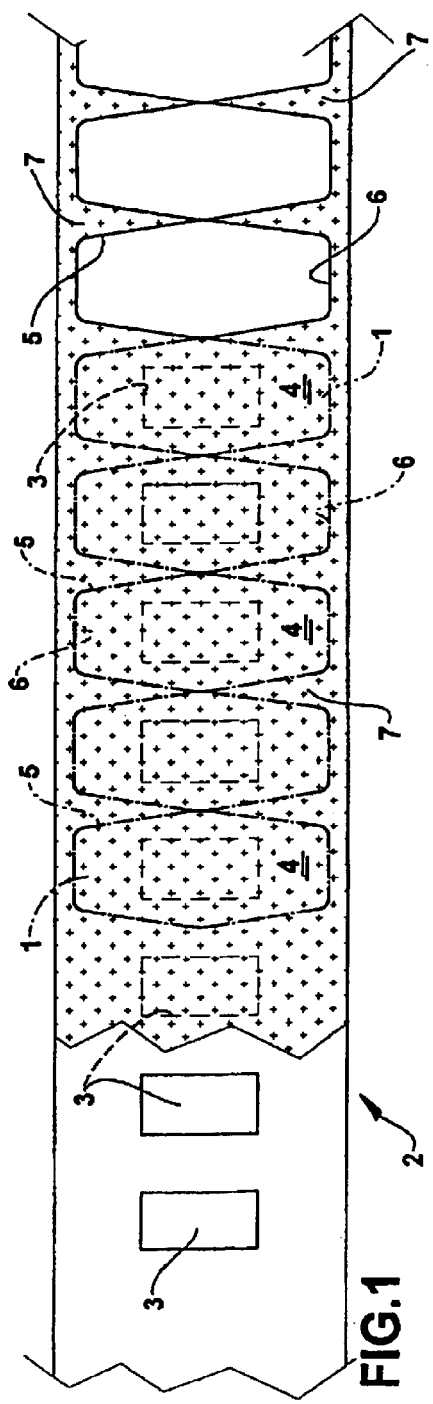
FIG. 2 illustrates, schematically, an upper plan view of a continuous strip, wherefrom are cut adhesive wound dressings, which are represented in said strip, before cutting, in dashed-dotted lines, according to the present invention.
Figure 3:
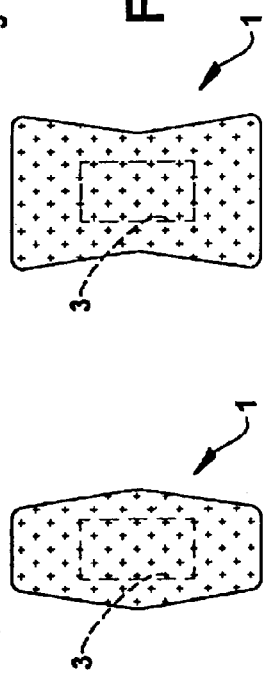
FIG. 3 illustrates, schematically, the adhesive wound dressings obtained by cutting the continuous strip illustrated in FIG. 2 and shaped as indicated by the dashed-dotted lines in said figure.

According to the present invention, the process for producing adhesive wound dressings minimizes the losses, due to the reduction of the useless strip marginal portions 7, when the adhesive wound dressings 1 have a non-rectangular contour. The present invention allows obtaining, from the same continuous strip 2 (FIG. 2), adhesive wound dressings 1 with different shapes relative to each other, as illustrated in FIG. 3.

The minimization of material losses of the present invention is achieved by a production process comprising a step of cutting, from said continuous strip 2, at least two different types of strip portions 4, which are dimensioned and shaped so that the strip marginal portions 7 be each incorporated as an integral part of a respective strip portion 4.

In the process of the present invention, the consecutive adjacent strip portions 4 of the prior art are spaced from each other in order to define, by increasing the distance therebetween, another strip portion 4 having a respective pad 3 and with a shape which complements the shape of each of the strip portions 4 spaced from each other. In this embodiment, each lateral edge 5 of the new strip portion 4 formed between two spaced apart strip portions 4 is common to the lateral edge 5 of the other adjacent spaced apart strip portion 4.

According to the present invention, from a predetermined type of strip portion 4, at least one second type of strip portion 4 is defined, which will be obtained during the cutting operation of the continuous strip 2, with a shape that will absorb substantially at least one of the marginal strip portions 7 of an adjacent strip portion 4, which has a common lateral edge 5 with said second type of strip portion 4. In a constructive option of the present invention, each of the strip portions 4 of another type different from the one which is predetermined as the principal type, incorporates the strip marginal portions 7 of each adjacent strip portion 4.

In the illustrated embodiment, between two strip portions 4 of the same predetermined and non-rectangular type, there are provided other two types of strip portions 4, each complementing a portion of the contour profile of another adjacent strip portion 4.

What is claimed is:

1. A process for producing adhesive wound dressings, from a continuous strip (2) in the form of a flexible adhesive film and affixing, along the extension of one of its faces, a plurality of pads (3), which are spaced from each other and aligned along the longitudinal axis of the continuous strip (2), each pad defining an adhesive wound dressing with a respective strip portion (4), each two adjacent strip portions (4) having a common lateral edge (5) and end edges (6) joining the lateral edges (5) of each strip portion (4), characterized in that said process comprises the step of cutting, from said continuous strip (2), at least two different types of strip portions (4), said strip portions dimensioned and shaped to each have a non rectangular contour.

2. Process, as in claim 1, characterized in that there is cut, from said continuous strip (2), between each two consecutive strip portions (4) of the same type, at least one strip portion (4) of another type.

3. Process, as in claim 2, characterized in that that there is a cut, from said continuous strip (2) between each two consecutive strip portions (4) of the same type, only one strip portion (4) of another type.

* * * * *